(12) United States Patent
Diodato

(10) Patent No.: US 12,295,894 B2
(45) Date of Patent: May 13, 2025

(54) SURGICAL TRACTION BOOT HAVING RESILIENT HEEL PAD AND MEDIAL AND LATERAL STRAPS

(71) Applicant: Allen Medical Systems, Inc., Batesville, IN (US)

(72) Inventor: Michael Philip Diodato, Fitchburg, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 307 days.

(21) Appl. No.: 17/952,472

(22) Filed: Sep. 26, 2022

(65) Prior Publication Data

US 2023/0141450 A1 May 11, 2023

Related U.S. Application Data

(60) Provisional application No. 63/277,256, filed on Nov. 9, 2021.

(51) Int. Cl.
*A61G 13/12* (2006.01)
*A61F 5/04* (2006.01)
(Continued)

(52) U.S. Cl.
CPC .......... *A61G 13/1245* (2013.01); *A61F 5/042* (2013.01); *A61G 7/0755* (2013.01);
(Continued)

(58) Field of Classification Search
CPC ............ A61G 13/1245; A61G 13/1205; A61G 13/12; A61G 7/0755; A61G 7/075; A61G 7/065; A61F 5/042; A61F 5/04
(Continued)

(56) References Cited

U.S. PATENT DOCUMENTS 542,390 A    7/1895  Linn
2,267,924 A  12/1941  Johnston
(Continued)

FOREIGN PATENT DOCUMENTS

CN    208725981 U    4/2019
CN    209203678 U    8/2019
(Continued)

OTHER PUBLICATIONS

PCT Search Report and Written Opinion for PCT/US2022/077566, dated Feb. 8, 2023, 13 pages.
(Continued)

*Primary Examiner* — Robert G Santos
(74) *Attorney, Agent, or Firm* — Barnes & Thornburg LLP

(57) ABSTRACT

A surgical boot apparatus for use in surgery involving hip distraction includes a boot shell having a sole portion configured for placement adjacent a sole of a foot of a patient and a calf portion configured for placement adjacent a calf of the patient. The boot shell has a heel-receiving opening located between the sole portion and the calf portion and configured for receipt of a heel of the patient. A resilient pad is provided having a main portion configured for engaging an Achilles area of the patient. The main portion includes an end region that extends into the heel-receiving opening. The end region has an end edge that includes a notch configured for receipt of a calcaneus of the patient.

19 Claims, 4 Drawing Sheets

(51) Int. Cl.
   *A61F 5/042* (2006.01)
   *A61G 7/075* (2006.01)
(52) U.S. Cl.
   CPC .............. *A61F 5/04* (2013.01); *A61G 7/075* (2013.01); *A61G 13/1205* (2013.01)
(58) Field of Classification Search
   USPC ........................... 5/640, 648, 651, 624, 621
   See application file for complete search history.

(56) References Cited

U.S. PATENT DOCUMENTS

| | | |
|---|---|---|
| 2,609,261 A | 9/1952 | Parker |
| 2,630,288 A | 3/1953 | Eubanks, Sr. |
| 2,732,269 A | 1/1956 | Astroff |
| 2,801,142 A | 7/1957 | Adams |
| 2,910,061 A | 10/1959 | Rabjohn |
| 3,226,105 A | 12/1965 | Weickgenannt et al. |
| 3,540,719 A | 11/1970 | Romney et al. |
| 3,762,514 A | 10/1973 | Freitag |
| 3,845,945 A | 11/1974 | Lawley et al. |
| 3,982,742 A | 9/1976 | Ford |
| 4,054,282 A | 10/1977 | Hamer |
| 4,160,332 A | 7/1979 | Salomon |
| 4,163,536 A | 8/1979 | Heller et al. |
| 4,180,254 A | 12/1979 | Lee et al. |
| 4,185,813 A | 1/1980 | Spann |
| 4,221,370 A | 9/1980 | Redwine |
| 4,252,306 A | 2/1981 | Johnson et al. |
| 4,323,060 A | 4/1982 | Pecheux |
| 4,367,869 A | 1/1983 | Dailey et al. |
| 4,373,709 A | 2/1983 | Whitt |
| 4,407,277 A | 10/1983 | Ellison |
| 4,418,900 A | 12/1983 | Ricke |
| 4,426,071 A | 1/1984 | Klevstad |
| 4,428,571 A | 1/1984 | Sugarman |
| 4,443,005 A | 4/1984 | Sugarman et al. |
| 4,467,538 A | 8/1984 | Olivieri |
| 4,471,952 A | 9/1984 | Spann |
| 4,482,138 A | 11/1984 | Spann |
| 4,526,355 A | 7/1985 | Moore et al. |
| 4,539,763 A | 9/1985 | Walkhoff |
| 4,545,573 A | 10/1985 | Murphy |
| 4,551,932 A | 11/1985 | Schoch |
| 4,564,164 A | 1/1986 | Allen et al. |
| 4,564,180 A | 1/1986 | Agee et al. |
| 4,573,482 A | 3/1986 | Williams, Jr. |
| 4,577,730 A | 3/1986 | Porter |
| 4,579,324 A | 4/1986 | Mcconnell |
| 4,620,698 A | 11/1986 | Reed et al. |
| 4,632,349 A | 12/1986 | Anstey |
| 4,681,309 A | 7/1987 | Lechner |
| 4,698,837 A | 10/1987 | Van Steenburg |
| 4,702,465 A | 10/1987 | Mcconnell |
| 4,724,626 A | 2/1988 | Baggio |
| 4,730,609 A | 3/1988 | Mcconnell |
| 4,732,145 A | 3/1988 | Latham |
| 4,766,892 A | 8/1988 | Kreitman |
| 4,782,827 A | 11/1988 | Paratte |
| 4,802,464 A | 2/1989 | Deprez |
| 4,807,618 A | 2/1989 | Auchinleck et al. |
| 4,809,687 A | 3/1989 | Allen |
| 4,827,496 A | 5/1989 | Cheney |
| 4,840,363 A | 6/1989 | Mcconnell |
| 4,886,258 A | 12/1989 | Scott |
| 4,893,419 A | 1/1990 | Arieh et al. |
| 4,898,491 A | 2/1990 | Van Steenburg |
| 4,909,264 A | 3/1990 | Wadsworth, III et al. |
| 4,913,413 A | 4/1990 | Raab |
| 4,940,218 A | 7/1990 | Akcelrod |
| 5,001,739 A | 3/1991 | Fischer |
| 5,010,900 A | 4/1991 | Auchinleck et al. |
| 5,020,525 A | 6/1991 | Ewing et al. |
| 5,027,799 A | 7/1991 | Laico et al. |
| 5,042,508 A | 8/1991 | Richard |
| 5,052,128 A | 10/1991 | Lonardo |
| 5,056,535 A | 10/1991 | Bonnell |
| 5,065,533 A | 11/1991 | Paris |
| 5,097,847 A | 3/1992 | Mikhail et al. |
| 5,104,363 A | 4/1992 | Shi |
| 5,116,008 A | 5/1992 | Allen |
| 5,177,882 A | 1/1993 | Berger |
| 5,249,377 A | 10/1993 | Walkhoff |
| 5,290,220 A | 3/1994 | Guhl |
| 5,291,903 A | 3/1994 | Reeves |
| 5,369,827 A | 12/1994 | Parke et al. |
| 5,410,769 A | 5/1995 | Waterman |
| 5,435,080 A | 7/1995 | Meiselman |
| 5,462,551 A | 10/1995 | Bailey et al. |
| 5,472,412 A | 12/1995 | Knoth |
| 5,481,770 A | 1/1996 | Ahlsten |
| 5,514,143 A | 5/1996 | Bonutti et al. |
| 5,515,562 A | 5/1996 | Miller et al. |
| 5,560,577 A | 10/1996 | Keselman |
| 5,582,379 A | 12/1996 | Keselman et al. |
| 5,608,934 A | 3/1997 | Torrie et al. |
| 5,636,899 A | 6/1997 | Schiff et al. |
| 5,645,079 A | 7/1997 | Zahiri et al. |
| 5,738,675 A | 4/1998 | Botimer |
| 5,758,374 A | 6/1998 | Ronci |
| 5,799,349 A | 9/1998 | Petersen |
| 5,802,641 A | 9/1998 | Van Steenburg |
| 5,806,117 A | 9/1998 | Gotfried |
| 5,918,330 A | 7/1999 | Navarro et al. |
| 5,937,546 A | 8/1999 | Messmer |
| 5,961,085 A | 10/1999 | Navarro et al. |
| 6,058,534 A | 5/2000 | Navarro et al. |
| 6,108,841 A | 8/2000 | Cameron et al. |
| 6,195,820 B1 | 3/2001 | Heimbrock et al. |
| 6,234,173 B1 | 5/2001 | Hajianpour |
| 6,263,531 B1 | 7/2001 | Navarro et al. |
| 6,289,537 B1 | 9/2001 | Hopper et al. |
| 6,289,558 B1 | 9/2001 | Hammerslag |
| 6,336,412 B2 | 1/2002 | Heimbrock et al. |
| 6,467,487 B1 | 10/2002 | Rios |
| 6,629,944 B2 | 10/2003 | Smart |
| 6,663,055 B2 | 12/2003 | Boucher et al. |
| 6,681,772 B2 | 1/2004 | Atwater et al. |
| 6,704,959 B2 | 3/2004 | Schuerch |
| 6,748,630 B2 | 6/2004 | Livingston |
| 6,811,541 B2 | 11/2004 | Lambert |
| 6,874,184 B2 | 4/2005 | Chandler |
| 7,210,252 B2 | 5/2007 | Morrow et al. |
| 7,243,654 B2 | 7/2007 | Schuerch |
| 7,316,040 B2 | 1/2008 | Siccardi et al. |
| 7,337,483 B2 | 3/2008 | Boucher et al. |
| 7,591,050 B2 | 4/2009 | Hammerslag |
| RE4,141 E | 7/2010 | Steenburg |
| 7,802,808 B2 | 9/2010 | Neiley |
| 7,832,401 B2 | 11/2010 | Torrie et al. |
| 7,870,624 B1 | 1/2011 | Winston |
| 7,947,006 B2 | 5/2011 | Torrie et al. |
| 8,332,977 B2 | 12/2012 | Bochner et al. |
| 8,707,486 B2 | 4/2014 | Chella et al. |
| RE4,606 E | 7/2016 | Torrie et al. |
| 9,635,906 B2 | 5/2017 | Midorikawa |
| 9,717,305 B2 | 8/2017 | Midorikawa |
| 9,951,904 B2 | 4/2018 | Perez et al. |
| 10,188,573 B2 | 1/2019 | Moriarty et al. |
| 10,478,364 B2 | 11/2019 | Fossez et al. |
| D878,836 S | 3/2020 | Kaiser et al. |
| 11,234,885 B2* | 2/2022 | Lane, II ............ A61G 13/1295 |
| 11,510,805 B2* | 11/2022 | Kaiser ............... A61G 13/1245 |
| 2004/0133979 A1 | 7/2004 | Newkirk et al. |
| 2007/0246914 A1* | 10/2007 | Neiley .................. A63C 10/06 |
| | | 280/624 |
| 2009/0235457 A1 | 9/2009 | Harvey |
| 2011/0023893 A1 | 2/2011 | Striggow et al. |
| 2012/0305006 A1 | 12/2012 | Keith-Lucas et al. |
| 2018/0221190 A1 | 8/2018 | Kaiser et al. |
| 2019/0240057 A1 | 8/2019 | Gunnsteinsson et al. |

(56) References Cited

U.S. PATENT DOCUMENTS

| | | | |
|---|---|---|---|
| 2019/0254905 A1 | 8/2019 | Haenel et al. | |
| 2020/0146863 A1 | 5/2020 | Shih | |
| 2023/0141450 A1* | 5/2023 | Diodato | ................ A61F 5/0195 5/640 |

FOREIGN PATENT DOCUMENTS

| | | | | |
|---|---|---|---|---|
| CN | 210121196 U | | 3/2020 | |
| CN | 210203541 U | | 3/2020 | |
| CN | 210698085 U | | 6/2020 | |
| CN | 210962495 U | | 7/2020 | |
| CN | 222130502 U | * | 12/2024 | ............ A61F 5/0111 |
| DE | 69629343 T2 | | 6/2004 | |
| DE | 202006006247 U1 | | 9/2006 | |
| WO | WO-2023086711 A1 | * | 5/2023 | ............ A61F 5/0111 |

OTHER PUBLICATIONS

Extended European Search Report issued on Jan. 24, 2025, in European Patent Application No. 22893753.8 (9 pages).

* cited by examiner

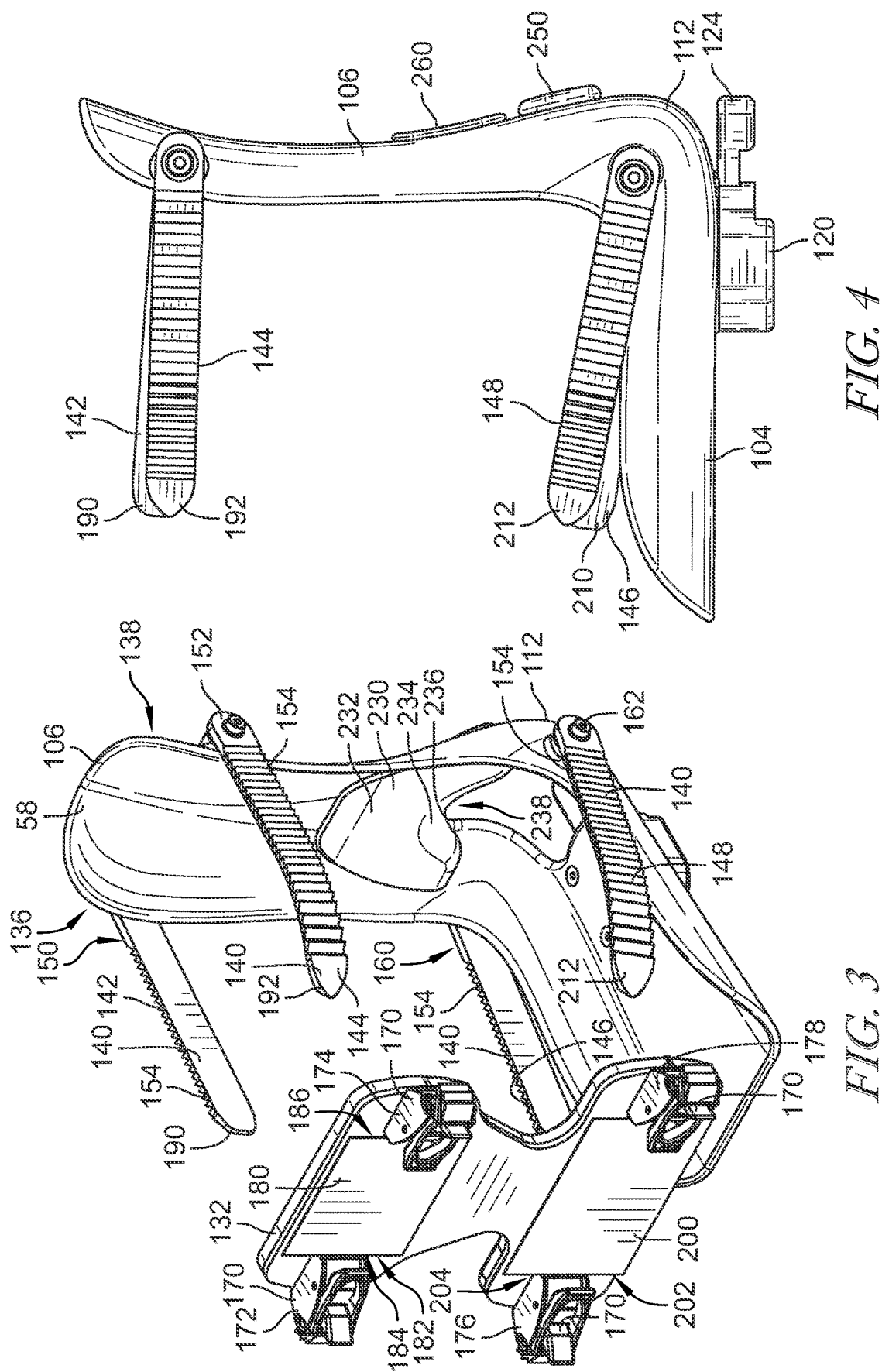

SURGICAL TRACTION BOOT HAVING RESILIENT HEEL PAD AND MEDIAL AND LATERAL STRAPS

CROSS-REFERENCE TO RELATED APPLICATIONS

This application claims priority under 35 U.S.C. § 119(e) to U.S. Provisional Application No. 63/277,256, filed Nov. 9, 2021, which is expressly incorporated by reference herein.

BACKGROUND

The present disclosure is related to a support apparatus for supporting a patient. More particularly, the present disclosure relates to a surgical boot apparatus for use in surgery involving hip distraction.

Often, when a patient is sedated for a surgery, the patient is supported by and secured to braces or supports coupled to a surgical table. Sometimes, unique supports are provided for a patient's extremities such as arm boards, leg supports, hand boards, stirrups, and boots. Supports known in the art sometimes secure patients to resist patient movement. Such supports can sometimes allow excessive patient movement relative to the supports. The position and orientation of supports is often adjusted during surgery to improve access to a surgical site or to move portions of the patient's body such as bones, muscles, tendons, and ligaments to evaluate the surgical results.

SUMMARY

The present disclosure includes one or more of the features recited in the appended claims and/or the following features which, alone or in any combination, may comprise patentable subject matter.

According to a first aspect of the disclosed embodiments, a surgical boot apparatus for use in surgery involving hip distraction includes a boot shell having a sole portion configured for placement adjacent a sole of a foot of a patient and a calf portion configured for placement adjacent a calf of the patient. The boot shell has a heel-receiving opening located between the sole portion and the calf portion and configured for receipt of a heel of the patient. The calf portion of the boot shell has a plug-receiving opening spaced from the heel-receiving opening. A resilient pad is provided having a main portion configured for engaging an Achilles area of the patient and a plug extending from the main portion. The plug is configured for press fitting into the plug-receiving opening of the boot shell to attach the resilient pad to the boot shell. The main portion includes an end region that extends into the heel-receiving opening. The end region has an end edge that includes a notch configured for receipt of a calcaneus of the patient.

In some embodiments of the first aspect, the plug of the resilient pad may be formed integrally with the main portion. The resilient pad may be made of silicone rubber.

Optionally, in the first aspect, the heel-receiving opening may be defined, in part, by a U-shaped edge of the calf portion of the boot shell. The resilient pad may include a U-shaped lip having a groove that receives the U-shaped edge of the calf portion. The U-shaped lip may be formed integrally with the main portion. The plug-receiving opening may be a triangular opening with rounded corners. A periphery of the plug may be triangular with rounded corners. The plug-receiving opening may be defined by an opening edge and the plug may have a peripheral wall formed with a groove that receives the opening edge. The heel-receiving opening and the plug receiving opening may be both centered on a longitudinal axis of the calf portion of the boot shell.

It may be desired, in the first aspect, that a first medial strap may be attached to the boot shell and a first lateral strap may be attached to the boot shell. An instep pad may have a first medial buckle configured for attachment to the first medial strap and a first lateral buckle configured for attachment to the first lateral strap. The first medial strap and the first lateral strap may each include a ladder strap. The ladder straps of the first medial strap and the first lateral strap may be of substantially equivalent lengths. The first medial buckle and the first lateral buckle may each include a ratchet buckle through which the respective ladder straps ratchet.

It may be contemplated, in the first aspect, that a second medial strap may be attached to the boot shell and a second lateral strap may be attached to the boot shell. The instep pad may further include a second medial buckle configured for attachment to the second medial strap and a second lateral buckle configured for attachment to the second lateral strap. The first medial strap, the first lateral strap, the second medial strap, and the second lateral strap may each include a ladder strap. The ladder straps of the second medial strap and the second lateral strap may be of substantially equivalent lengths. The ladder straps of the first medial strap, the second medial strap, the first lateral strap, and the second lateral strap may be of substantially equivalent lengths. The second medial buckle and the second lateral buckle may each be ratchet buckles through which the ladder straps of the second medial strap and the second lateral strap ratchet. Proximal ends of the first medial strap and the first lateral strap may be attached to the calf portion of the boot shell. Proximal ends of the second medial strap and the second lateral strap may be attached to a junction region of the boot shell where the sole portion and calf portion meet.

In some embodiments of the first aspect, the instep pad may have a first pocket situated between the first medial buckle and the first lateral buckle. The first pocket may have open sides. Distal ends of the first medial strap and the first lateral strap may be insertable into the first pocket through the open sides of the first pocket to retain the distal ends of the first medial strap and the first lateral strap against the instep pad during surgery. The instep pad may have a second pocket situated between the first medial buckle and the first lateral buckle. The second pocket may have open sides. Distal ends of the second medial strap and the second lateral strap may be insertable into the second pocket through the open sides of the second pocket to retain the distal ends of the second medial strap and the second lateral strap against the instep pad during surgery. The instep pad may include a leg-engaging portion that is generally hour glass shaped. A first patch may be coupled to the leg-engaging portion. A second patch may be coupled to the leg-engaging portion. The first pocket may be defined between the first patch and the leg-engaging portion. The second pocket may be defined between the second patch and the leg-engaging portion.

According to a second aspect of the disclosed embodiments, a surgical boot apparatus for use in surgery involving hip distraction includes a boot shell having a sole portion configured for placement adjacent a sole of a foot of a patient and a calf portion configured for placement adjacent a calf of the patient. Four ladder straps are coupled to the boot shell. The four ladder straps include a first medial strap, a first lateral strap, a second medial strap, and a second lateral strap. An instep pad has four ratchet buckles to interface with the respective ladder straps. The ratchet buckles are operable to tighten the instep pad against the patient's leg when the patient's leg is situated within the boot shell. The ratchet buckles are movable to a released state to permit the instep pad to be completely detached from the four ladder straps.

In some embodiments of the second aspect, the ladder straps of the first medial strap and the first lateral strap may be of substantially equivalent lengths. The ladder straps of the second medial strap and the second lateral strap may be of substantially equivalent lengths. The ladder straps of the first medial strap, the second medial strap, the first lateral strap, and the second lateral strap may be of substantially equivalent lengths. Proximal ends of the first medial strap and the first lateral strap may be attached to the calf portion of the boot shell. Proximal ends of the second medial strap and the second lateral strap may be attached to a junction region of the boot shell where the sole portion and calf portion meet.

Optionally, in the second aspect, the instep pad may have a first pocket situated between the first medial buckle and the first lateral buckle. The first pocket may have open sides. Distal ends of the first medial strap and the first lateral strap may be insertable into the first pocket through the open sides of the first pocket to retain the distal ends of the first medial strap and the first lateral strap against the instep pad during surgery. The instep pad may have a second pocket situated between the first medial buckle and the first lateral buckle. The second pocket may have open sides. Distal ends of the second medial strap and the second lateral strap may be insertable into the second pocket through the open sides of the second pocket to retain the distal ends of the second medial strap and the second lateral strap against the instep pad during surgery.

It may be desired, in the second aspect, that the instep pad may include a leg-engaging portion that is generally hour glass shaped. A first patch may be coupled to the leg-engaging portion. A second patch may be coupled to the leg-engaging portion. The first pocket may be defined between the first patch and the leg-engaging portion. The second pocket may be defined between the second patch and the leg-engaging portion. Each ladder strap may have a proximal end that is pinned to boot shell to permit each ladder strap to rotate relative to the boot shell about a respective pivot axis.

It may be contemplated, in the second aspect, that the boot shell may include a heel-receiving opening located between the sole portion and the calf portion and configured for receipt of a heel of the patient. The calf portion of the boot shell may have a plug-receiving opening spaced from the heel-receiving opening. A resilient pad may have a main portion configured for engaging an Achilles area of the patient. A plug may extend from the main portion. The plug may be configured for press fitting into the plug-receiving opening of the boot shell to attach the resilient pad to the boot shell. The main portion may include an end region that extends into the heel-receiving opening. The end region may have an end edge including a notch configured for receipt of a calcaneus of the patient.

In some embodiments of the second aspect, the plug of the resilient pad may be formed integrally with the main portion. The resilient pad may be made of silicone rubber. The heel-receiving opening may be defined, in part, by a U-shaped edge of the calf portion of the boot shell. The resilient pad may include a U-shaped lip having a groove that receives the U-shaped edge of the calf portion. The U-shaped lip may be formed integrally with the main portion. The plug-receiving opening may be a triangular opening with rounded corners. A periphery of the plug may be triangular with rounded corners. The plug-receiving opening may be defined by an opening edge. The plug may have a peripheral wall formed with a groove that receives the opening edge. The heel-receiving opening and the plug receiving opening may be both centered on a longitudinal axis of the calf portion of the boot shell. A mount may be attached to an underside of the sole portion. The mount may be configured to lock the boot shell to a hip distractor. The mount may include a release input that is movable to unlock the boot shell from the hip distractor to permit the surgical boot apparatus to be detached from the hip distractor.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION

The detailed description particularly refers to the accompanying figures in which:

FIG. 3 is an exploded front perspective view of the boot shell and the leg-engaging portion of the instep pad of the surgical boot apparatus shown in FIG. 2;

FIG. 4 is a side elevation view of the boot shell shown in FIG. 3;

DETAILED DESCRIPTION

Figure 1:
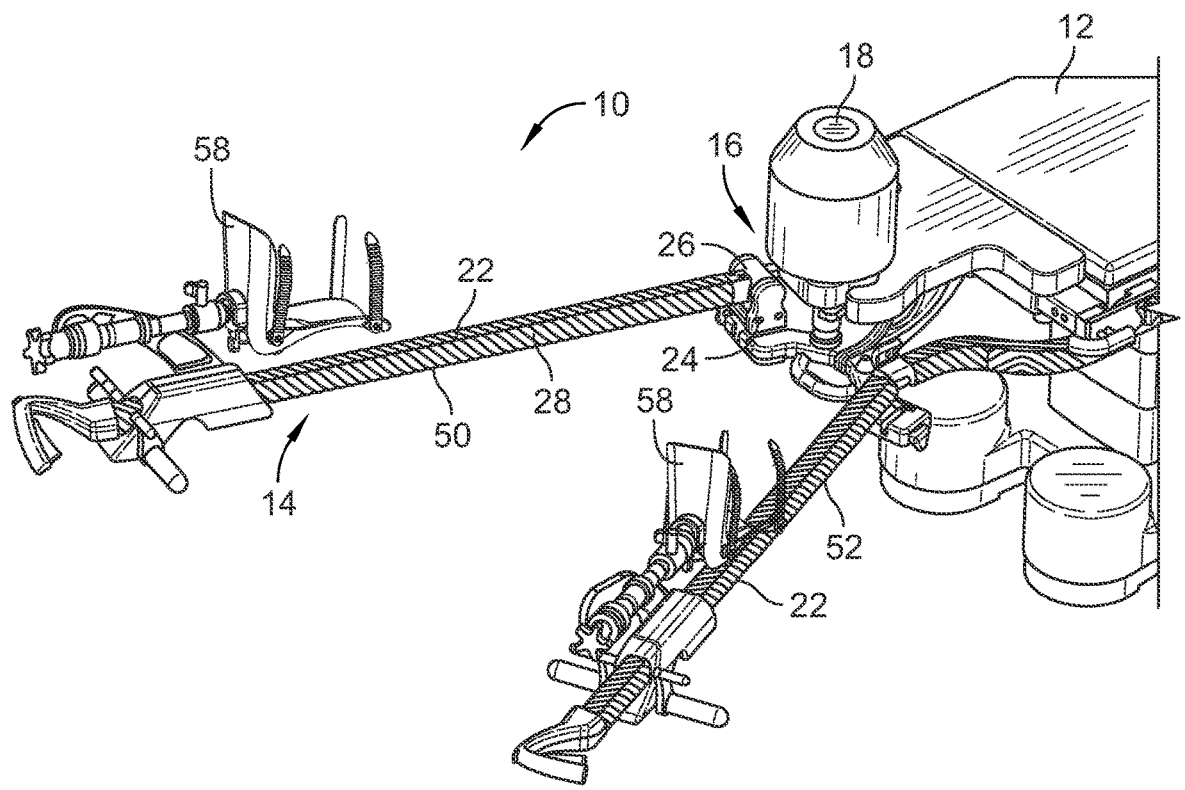
FIG. 1 is a perspective view of a patient support apparatus including a limb-support unit according to the present disclosure.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a support apparatus 10 includes, for example, a surgical table 12 and a limb-support unit 14 which is embodied as a hip distractor. The limb-support unit 14 is coupled to a foot end 16 of the surgical table 12. In an example of use, the limb-support unit 14 supports a patient's legs and the surgical table 12 supports a patient's upper body. The limb-support unit 14 may be used to place tension on the patient's legs during surgery. This is also known as placing the patient's legs in traction. During a hip-replacement surgery, the patient's leg in which the hip is being replaced may need to be repositioned during the surgery to provide the surgeon with improved access while maintaining the patient's leg in traction. The limb-support unit 14 in accordance with the present disclosure provides the ability to reposition the patient's leg while maintaining that leg in traction. The limb support unit 14 is further configured to apply sufficient force on the patient's leg during hip distraction to pull the hip joint out of socket (i.e., pull the femoral head out of the acetabulum).

The limb-support unit 14 includes a countertraction unit 18, such as a padded perineal post, and leg holders 22 that each support a boot shell 58 in the illustrative example. The countertraction unit 18 is coupled to the foot end 16 of the surgical table 12 in a fixed position. The leg holders 22 are coupled in spaced-apart relation to the countertraction unit 18. A moveable leg holder 50 moves relative to the countertraction unit 18 as suggested in FIG. 1. The moveable leg holder 50 includes a joint mount 24, a multi-axis joint 26, and a spar 28. The joint mount 24 is coupled to the countertraction unit 18 in a fixed position while the limb-support unit 14 supports portions of the patient. The multi-axis joint 26 is arranged to interconnect the spar 28 and the joint mount 24 to cause the spar 28 to move relative to the joint mount 24. The spar 28 is coupled to the multi-axis joint 26 and arranged to extend away from the multi-axis joint 26 to support the patient's leg in traction during surgery involving hip distraction. A stationary leg holder 52 is stationary and is supported by an accessory rail at the side of the table 12 and the limb-support unit 14 to which the countertraction unit 18 and multi-axis joint 26 are also coupled. The stationary leg holder 52 is detachable from the limb-support unit 14 and surgical table accessory rail; however, in use during surgery, the stationary leg holder 52 is stationary.

Figure 2:
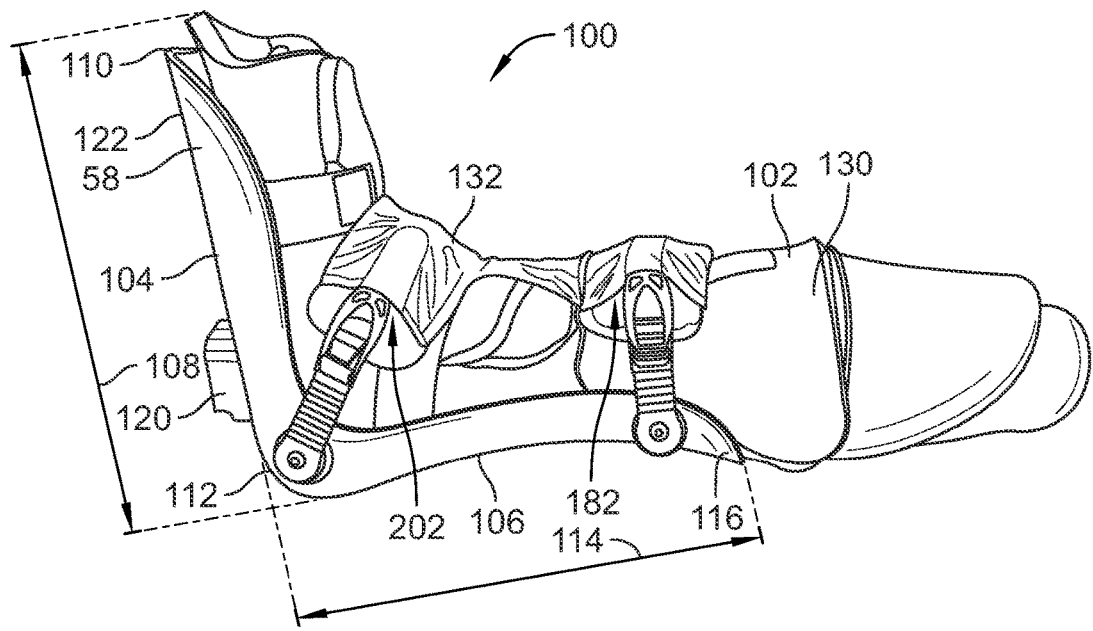
FIG. 2 is a side view of a surgical boot apparatus for use with the patient support apparatus shown in FIG. 1 during surgery involving hip distraction.

Referring to FIG. 2, a surgical boot apparatus 100 for use in surgery involving hip distraction includes the boot shell 58 and an instep pad 102 positioned in the boot shell 58 and secured to the boot shell 58. The boot shell 58 may be formed from plastic, composites, aluminum, or any other suitable material for supporting a patient's foot during surgery. The boot shell 58 includes a sole portion 104 configured for placement adjacent a sole of the foot of a patient and a calf portion 106 configured for placement adjacent a calf of the patient. The sole portion 104 extends along a longitudinal axis 108 from an end 110 to a junction region 112 of the boot shell 58 where the sole portion 104 and calf portion 106 meet. The calf portion 106 extends along a longitudinal axis 114 from an end 116 to the junction region 112. The longitudinal axis 108 extends at an angle relative to the longitudinal axis 114. In some embodiments, the longitudinal axis 108 extends at an orthogonal angle relative to the longitudinal axis 114. In some embodiments, the longitudinal axis 108 extends at a non-orthogonal angle relative to the longitudinal axis 114. In some embodiments, the longitudinal axis 108 extends at an acute angle relative to the longitudinal axis 114. In some embodiments, the longitudinal axis 108 extends at an obtuse angle relative to the longitudinal axis 114.

A mount 120 is attached to an underside 122 of the sole portion 104. The mount 120 extends from the sole portion 104 is a direction opposite the calf portion 106. The mount 120 is configured to lock the boot shell 58 to the hip distractor 10. That is, the mount 120 is configured to lock the boot shell 58 to one of the leg holders 22 of the hip distractor. As seen in FIG. 4, the mount 120 includes a release input 124 that is movable to unlock the boot shell 58 from the hip distractor 10 to permit the surgical boot apparatus 100 to be detached from the hip distractor 10. In the illustrative example, surgical boot apparatus 100, and particularly mount 120 of surgical boot apparatus 100, is configured for mounting to a model no. AR-6529S Arthrex Hip Distraction System (HDS) available from Arthrex Inc. of Naples, Florida Additional details of mount 120 are shown and described in U.S. Pat. No. 9,381,130 which is hereby incorporated herein by reference to the extent not inconsistent with the present disclosure which shall control as to any inconsistencies (see particularly FIGS. 6-8 of the '130 patent and the related discussion of quick disconnect receiver 15). In other embodiments, mount 120 is configured for connection to hip distraction systems of other manufacturers such as the Maquet subsidiary of Getinge AB, Steris Corporation, and Smith & Nephew PLC, just to name a few.

A leg wrap 130 is configured wrap around the foot of the patient and at least partially around the calf of the patient. The leg wrap 130 is configured to be positioned within the boot shell 58. The leg wrap 130 is formed from a disposable material that facilitates providing comfort to the patient, for example, foam, while the patient's foot is inserted into the boot shell 58. Other materials may be contemplated. The material may also be selected to warm the patient's foot during surgery. The instep pad 102 includes a leg engaging portion 132 that positions over the leg wrap 130 and is configured to secure the patient's foot within the surgical boot apparatus 100, as described below.

Referring now to FIG. 3, the boot shell 58 includes a medial side 136 and an opposite lateral side 138. For reference, the medial side 136 is positioned adjacent a midline of the patient. That is, with respect to the hip distractor 10, the medial side 136 is positioned adjacent a centerline of the hip distractor 10. The lateral side 138 is positioned away from the midline of the patient. With respect to the hip distractor 10, the lateral side 138 is positioned away from the centerline of the hip distractor 10. In some embodiments, the surgical boot apparatus 100 is symmetrical about a centerline between the medial side 136 and the lateral side 138. Four straps 140 are coupled to and extend from the boot shell 58. The four straps 140 including a first medial strap 142, a first lateral strap 144, a second medial strap 146, and a second lateral strap 148.

Figure 6:
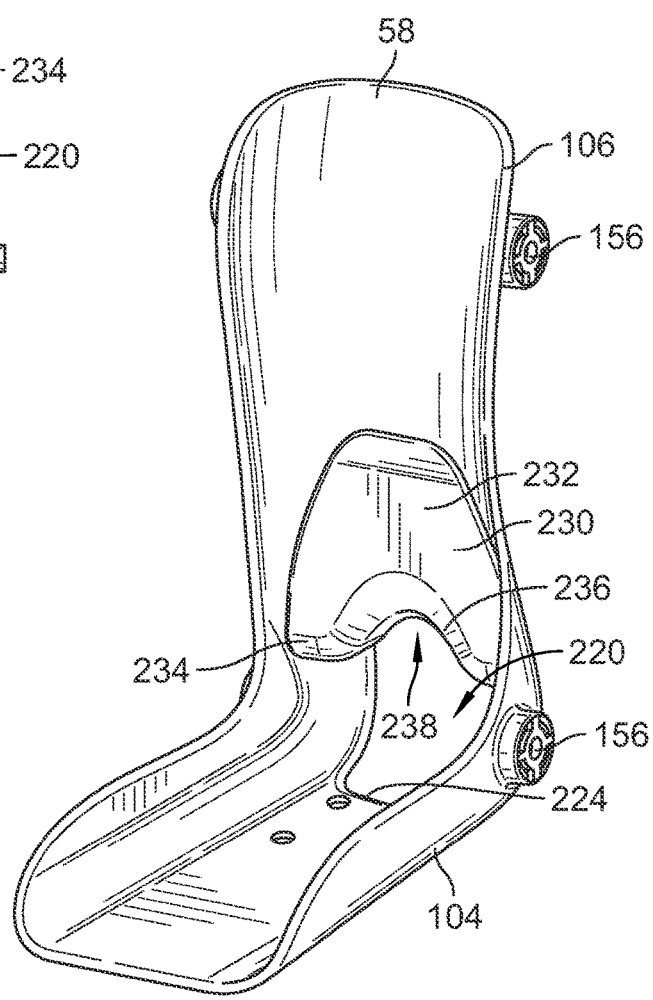
FIG. 6 is a front perspective view of the boot shell shown in FIG. 3.
Figures 7, 8:
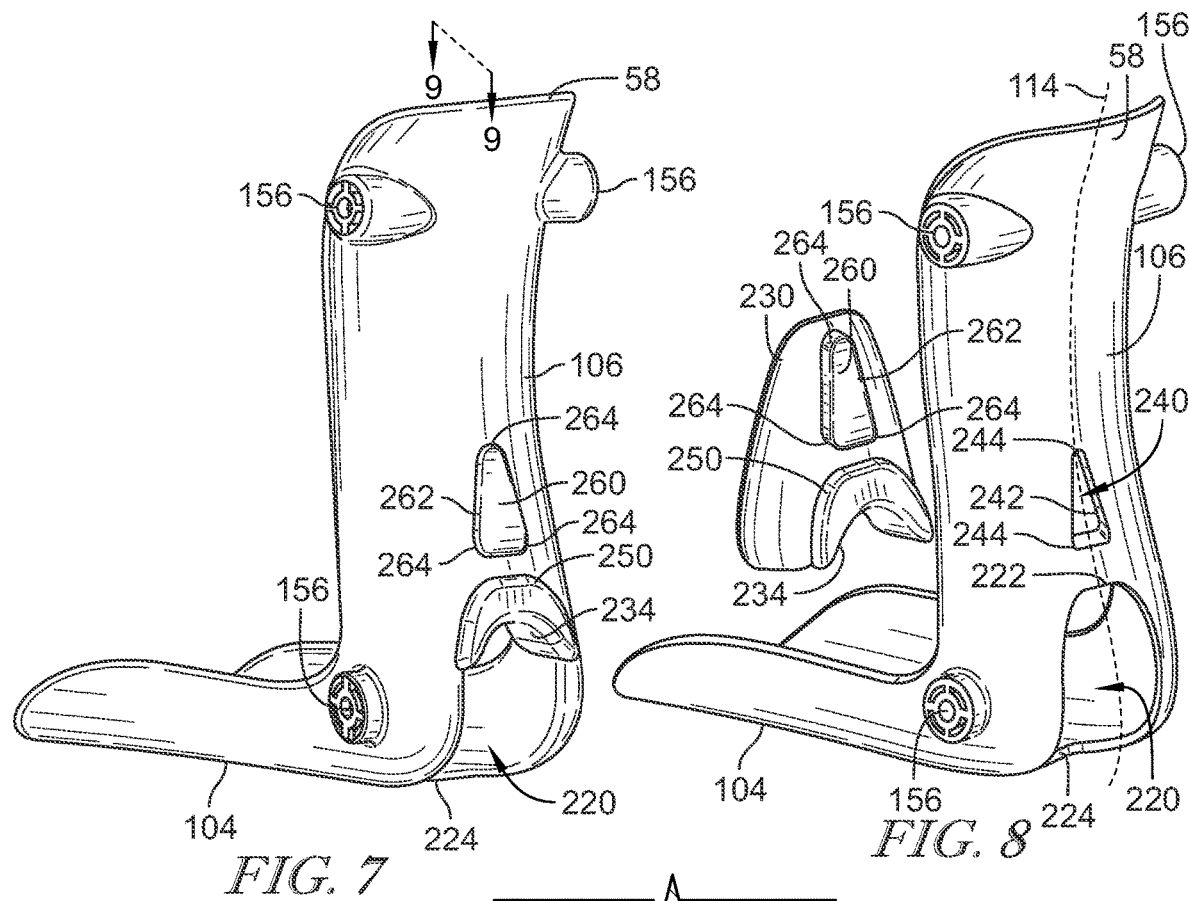
FIG. 7 is a rear perspective view of the boot shell shown in FIG. 3 with a resilient heel pad inserted into the boot shell.
FIG. 8 is an exploded rear perspective view of the boot shell and the resilient heel pad shown in FIG. 7.

A proximal end 150 of the first medial strap 142 is attached to the calf portion 106 of the boot shell 58 on the medial side 136. A proximal end 152 of the first lateral strap 144 is also attached to the calf portion 106 of the boot shell 58 on the lateral side 138. Referring to FIGS. 6-8, the boot shell 58 includes a plurality of pivot points 156. The proximal end 150 of the first medial strap 142 and the proximal end 152 of the first lateral strap 144 are pinned to a respective pivot point 156 to permit the first medial strap 142 and the first lateral strap 144 to rotate relative to the boot shell 58 about a respective pivot axis. The first medial strap 142 and the first lateral strap 144 are each embodied as a ladder strap that includes a plurality of ridges 154 to enable the strap to be ratcheted through a buckle, as described below. In some embodiments, other types of straps are used in lieu of ladder straps 142, 144, 146, 148. In the illustrative embodiment, the first medial strap 142 and the first lateral strap 144 are of substantially equivalent lengths. It will be appreciated that the first medial strap 142 and the first lateral strap 144 may have different lengths in other embodiments.

A proximal end 160 of the second medial strap 146 is attached to the junction region 112 of the boot shell 58 on the medial side 136. A proximal end 162 of the second lateral strap 148 is also attached to the junction region 112 of the boot shell 58 on the lateral side 138. Referring to FIGS. 6-8, the proximal end 160 of the second medial strap 146 and the proximal end 162 of the second lateral strap 148 are pinned to a respective pivot point 156 to permit the second medial strap 146 and the second lateral strap 148 to rotate relative to the boot shell 58 about a respective pivot axis. The second medial strap 146 and the second lateral strap 148 are each embodied as a ladder strap that includes a plurality of ridges 154 to enable the strap to be ratcheted through a buckle, as described below. In some embodiments, other straps may be contemplated. In the illustrative embodiment, the second medial strap 146 and the second lateral strap 148 are of substantially equivalent lengths. It will be appreciated that the second medial strap 146 and the second lateral strap 148 may have different lengths in other embodiments. In some embodiments, the first medial strap 142, the second medial strap 146, the first lateral strap 144, and the second lateral strap 148 are of substantially equivalent lengths.

When it is stated herein that straps 142, 144, 146, 148 are of "substantially" equivalent lengths, it is intended to cover lengths that are within +/−10% of each other. For example, if a strap is 10 inches in length, then straps that are 9 inches to 11 inches in length are considered to be of substantially length to the 10-inch strap. That is, 10% of 10 inches is 1 inch. This is given as just one arbitrary example and is not intended to imply that any of straps 142, 144, 146, 148 are ten inches in length, but it is not intended to rule out such a possibility either.

The leg-engaging portion 132 of the instep pad 102 is generally hour glass shaped. Four buckles 170 are provided on the leg-engaging portion 132 of the instep pad 102 to interface with a respective strap 140. The buckles 170 are operable to tighten the instep pad 102 against the patient's leg when the patient's leg is situated within the boot shell 58. The buckles 170 are movable to a released state to permit the instep pad 102 to be completely detached from the four straps 140.

A first medial buckle 172 is configured for attachment to the first medial strap 142. A first lateral buckle 174 is configured for attachment to the first lateral strap 144. The first medial buckle 172 and the first lateral buckle 174 are each embodied as a ratchet buckle through which the respective first medial ladder strap 142 and first lateral ladder strap 144 are ratcheted. A second medial buckle 176 is configured for attachment to the second medial strap 146. A second lateral buckle 178 is configured for attachment to the second lateral strap 148. The second medial buckle 176 and the second lateral buckle 178 are each embodied as a ratchet buckle through which the respective second medial ladder strap 146 and second lateral ladder strap 148 are ratcheted.

A first patch 180 is coupled to the leg-engaging portion 132 to define a first pocket 182 (shown in FIG. 2) between the first patch 180 and the leg-engaging portion 132. The first pocket 182 is situated between the first medial buckle 172 and the first lateral buckle 174. The first pocket 182 includes open medial side 184 and an open lateral side 186. A distal end 190 of the first medial strap 142 is insertable into the first pocket 182 through the open medial side 184 of the first pocket 182 to retain the distal end 190 of the first medial strap 142 against the instep pad 102 during surgery. A distal end 192 of the first lateral strap 144 is insertable into the first pocket 182 through the open lateral side 186 of the first pocket 182 to retain the distal end 192 of the first lateral strap 144 against the instep pad 102 during surgery.

A second patch 200 is coupled to the leg-engaging portion 132 to define a second pocket 202 (shown in FIG. 2) between the second patch 200 and the leg-engaging portion 132. The second pocket 202 is situated between the second medial buckle 176 and the second lateral buckle 178. The second pocket 202 includes open medial side 204 and an open lateral side 206. A distal end 210 (shown in FIG. 4) of the second medial strap 146 is insertable into the second pocket 202 through the open medial side 204 of the second pocket 202 to retain the distal end 210 of the second medial strap 146 against the instep pad 102 during surgery. A distal end 212 of the second lateral strap 148 is insertable into the second pocket 202 through the open lateral side 206 of the second pocket 202 to retain the distal end 212 of the second lateral strap 148 against the instep pad 102 during surgery.

Figure 5:
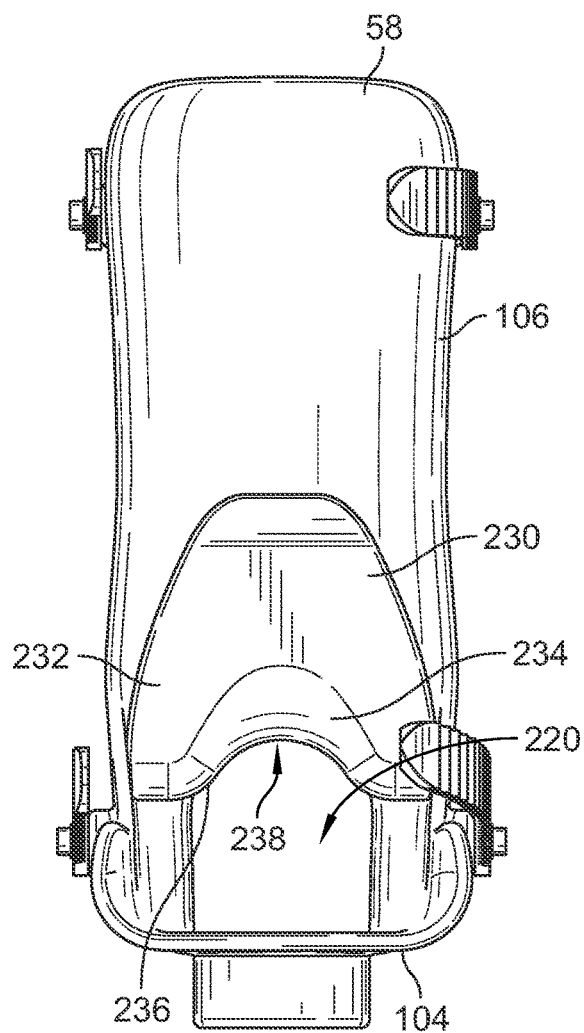
FIG. 5 is a front elevation view of the boot shell shown in FIG. 3.

Referring to FIGS. 5 and 6, the boot shell 58 includes a heel-receiving opening 220. The heel-receiving opening 220 extends entirely through the boot shell 58. The heel-receiving opening 220 is located between the sole portion 104 and the calf portion 106 of the boot shell 58. That is, the heel-receiving opening 220 extends partially through the sole portion 104 of the boot shell 58 and partially through the calf portion 106 of the boot shell 58. The heel-receiving opening 220 is configured to receive a heel of the patient. Accordingly, when the patient's foot is positioned in the boot shell 58, the heel of the patient positions within the heel-receiving opening 220.

A resilient pad 230 is positioned in the calf portion 106 of the boot shell 58. In some embodiments, the resilient pad 230 is made of silicone rubber. It will be appreciated that other suitable materials may be used to form the resilient pad 230. In some embodiments, the resilient pad 230 is molded. For example, the resilient pad 230 may be molded to a specific patient's heel. The resilient pad 230 includes a main portion 232 that is configured for engaging an Achilles area of the patient's foot. The main portion 232 includes an end region 234 having a U-shaped end edge 236. The U-shaped end edge 236 includes a notch 238 configured for receipt of a calcaneus of the patient's foot. The notch 238 is tapered from the main portion 232 to the U-shaped end edge 236.

Referring now to FIGS. 7 and 8, the heel-receiving opening 220 is defined, in part, by a U-shaped edge 222 of the calf portion 106 of the boot shell 58. The heel-receiving opening 220 is further defined, in part, by a linear edge 224 of the sole portion 104 of the boot shell 58, as seen more clearly in FIG. 6. The heel-receiving opening 220 extends between the U-shaped edge 222 and the linear edge 224.

Figure 9:
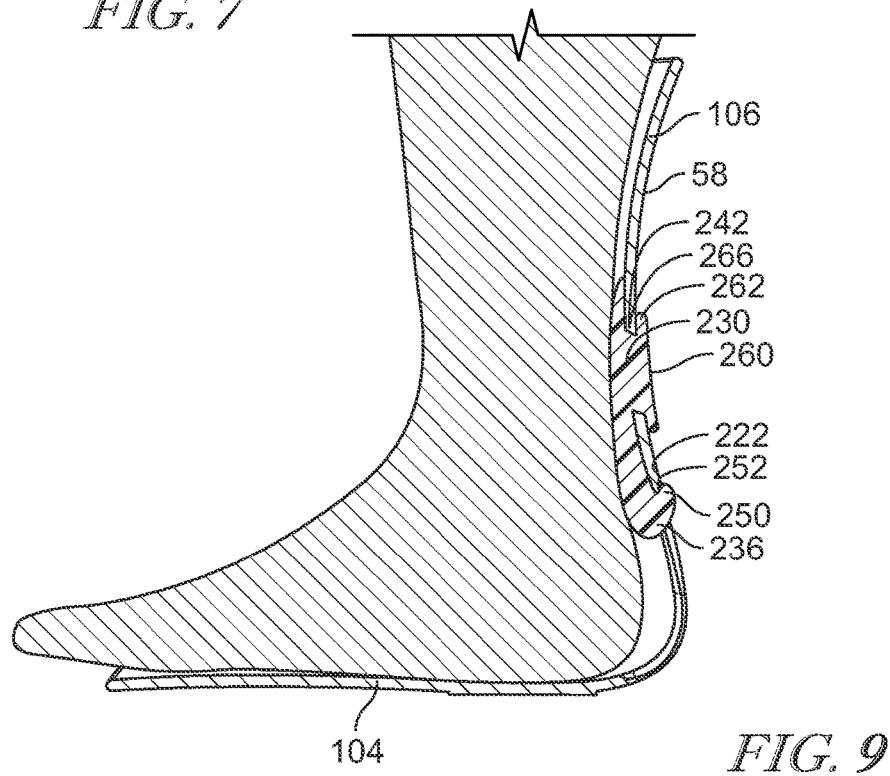
FIG. 9 is a cross-sectional view of the boot shell and the resilient pad taken along line 9-9 shown in FIG. 7 and having a foot positioned in the boot shell without the leg wrap shown in FIG. 2.

The end region 234 of the resilient pad 230 extends into the heel-receiving opening 220. The resilient pad 230 includes a U-shaped lip 250 extending along the U-shaped end edge 236 and having a groove 252. In some embodiments, the U-shaped lip 250 is formed integrally with the main portion 232 of the resilient pad 230. The groove 252 is configured to receive the U-shaped edge 222 of the calf portion 106 to attach the resilient pad 230 to the boot shell 58, as illustrated in FIG. 9. It should be noted that, in FIG. 9, the patient's foot is shown without the leg wrap 130, shown FIG. 2. The diagrammatic image of the foot and lower leg in FIG. 9 is intended to include the leg wrap 130, but optionally, the leg wrap 130 can be omitted.

The calf portion 106 of the boot shell 58 also includes a plug-receiving opening 240 spaced from the heel-receiving opening 220. In some embodiments, the heel-receiving opening 220 and the plug receiving opening 240 are both centered on the longitudinal axis 114 of the calf portion 106 of the boot shell 58, as illustrated in FIG. 8. The plug-receiving opening 240 includes a triangular opening defined by an opening edge 242 having rounded corners 244. It will be appreciated that the plug-receiving opening 240 may have other shapes in other embodiments.

A plug 260 extends from the main portion 232 of resilient pad 230. In some embodiments, the plug 260 of the resilient pad 230 is formed integrally with the main portion 232 of the resilient pad 230. In other embodiments, the plug 260 may be formed separately from the main portion 232 of the resilient pad 230. A peripheral wall 262 of the plug 260 is generally triangular with rounded corners 264. It will be appreciated that the plug 260 may have other shapes in other embodiments. The plug 260 is generally sized and shaped to the plug-receiving opening 240. The plug 260 is configured for press fitting into the plug-receiving opening 240 of the boot shell 58 to attach the resilient pad 230 to the boot shell 58. The peripheral wall 262 includes a groove 266 that is configured to receive the opening edge 242 of the plug-receiving opening 240 of the calf portion 106 to attach the resilient pad 230 to the boot shell 58, as illustrated in FIG. 9.

During use of the surgical boot apparatus 100, traction pulls the calcaneus of the patient's foot into contact with the resilient pad 230 to prevent heel lift. It should be noted that with the leg wrap 130 present on the patient's foot, the calcaneus does not directly contact the resilient pad 230. Rather, the leg wrap 130 is positioned between the calcaneus and the resilient pad 230. In some embodiments, the resilient pad 230 comfortably captures the top of the patient's calcaneus to create a strong hold while reducing the risk of pressure injury. In some embodiments, the leg-engaging portion 132 of the instep pad 102 conforms to the top of the patient's ankle and lower shin. The leg-engaging portion 132 of the instep pad 102 has ratcheting buckles 170 at the top and bottom of the pad 102 on the lateral and medial side of the patient's leg to keep the pad 102 centered on the patient's leg/foot and to create symmetrical pressure to pull the heel back into the boot shell 58. This pressure forces the heel to be captured by the resilient pad 230.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used, the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles have been presented, they need not be utilized in combination, and many combinations of aspects and principles are possible in light of the various embodiments provided above.

The invention claimed is:

1. A surgical boot apparatus for use in surgery involving hip distraction, the surgical boot apparatus comprising:
   a boot shell having a sole portion configured for placement adjacent a sole of a foot of a patient and a calf portion configured for placement adjacent a calf of the patient, the boot shell having a heel-receiving opening located between the sole portion and the calf portion and configured for receipt of a heel of the patient, the calf portion of the boot shell having a plug-receiving opening spaced from the heel-receiving opening, and
   a resilient pad having a main portion configured for engaging an Achilles area of the patient and a plug extending from the main portion, the plug being configured for press fitting into the plug-receiving opening of the boot shell to attach the resilient pad to the boot shell, the main portion including an end region that extends into the heel-receiving opening, and the end region having an end edge including a notch configured for receipt of a calcaneus of the patient,
   wherein the heel-receiving opening is defined, in part, by a U-shaped edge of the calf portion of the boot shell and wherein the resilient pad includes a U-shaped lip having a groove that receives the U-shaped edge of the calf portion.

2. The surgical boot apparatus of claim 1, wherein the plug of the resilient pad is formed integrally with the main portion.

3. The surgical boot apparatus of claim 1, wherein the resilient pad is made of silicone rubber.

4. The surgical boot apparatus of claim 1, wherein:
   the plug-receiving opening is a triangular opening with rounded corners; and
   a periphery of the plug is triangular with rounded corners.

5. The surgical boot apparatus of claim 1, wherein the heel-receiving opening and the plug-receiving opening are both centered on a longitudinal axis of the calf portion of the boot shell.

6. The surgical boot apparatus of claim 1, further comprising a first medial strap attached to the boot shell and a first lateral strap attached to the boot shell and further comprising an instep pad having a first medial buckle configured for attachment to the first medial strap and a first lateral buckle configured for attachment to the first lateral strap.

7. The surgical boot apparatus of claim 6, wherein the first medial strap and the first lateral strap each comprise a ladder strap.

8. The surgical boot apparatus of claim 7, wherein the ladder straps of the first medial strap and the first lateral strap are of substantially equivalent lengths.

9. The surgical boot apparatus of claim 7, wherein the first medial buckle and the first lateral buckle each comprises a ratchet buckle through which the respective ladder straps ratchet.

10. The surgical boot apparatus of claim 6, further comprising a second medial strap attached to the boot shell and a second lateral strap attached to the boot shell and wherein the instep pad further includes a second medial buckle configured for attachment to the second medial strap and a second lateral buckle configured for attachment to the second lateral strap.

11. The surgical boot apparatus of claim 10, wherein the first medial strap, the first lateral strap, the second medial strap, and the second lateral strap each comprise a ladder strap.

12. The surgical boot apparatus of claim 11, wherein the ladder straps of the second medial strap and the second lateral strap are of substantially equivalent lengths.

13. The surgical boot apparatus of claim 11, wherein the ladder straps of the first medial strap, the second medial strap, the first lateral strap, and the second lateral strap are of substantially equivalent lengths.

14. The surgical boot apparatus of claim 11, wherein the second medial buckle and the second lateral buckle are each ratchet buckles through which the ladder straps of the second medial strap and the second lateral strap ratchet.

15. A surgical boot apparatus for use in surgery involving hip distraction, the surgical boot apparatus comprising:
  a boot shell having a sole portion configured for placement adjacent a sole of a foot of a patient and a calf portion configured for placement adjacent a calf of the patient, the boot shell having a heel-receiving opening located between the sole portion and the calf portion and configured for receipt of a heel of the patient, the calf portion of the boot shell having a plug-receiving opening spaced from the heel-receiving opening, and
  a resilient pad having a main portion configured for engaging an Achilles area of the patient and a plug extending from the main portion, the plug being configured for press fitting into the plug-receiving opening of the boot shell to attach the resilient pad to the boot shell, the main portion including an end region that extends into the heel-receiving opening, and the end region having an end edge including a notch configured for receipt of a calcaneus of the patient,
  wherein the plug-receiving opening is defined by an opening edge and the plug has a peripheral wall formed with a groove that receives the opening edge.

16. A surgical boot apparatus for use in surgery involving hip distraction, the surgical boot apparatus comprising:
  a boot shell having a sole portion configured for placement adjacent a sole of a foot of a patient and a calf portion configured for placement adjacent a calf of the patient, the boot shell having a heel-receiving opening located between the sole portion and the calf portion and configured for receipt of a heel of the patient, the calf portion of the boot shell having a plug-receiving opening spaced from the heel-receiving opening,
  a resilient pad having a main portion configured for engaging an Achilles area of the patient and a plug extending from the main portion, the plug being configured for press fitting into the plug-receiving opening of the boot shell to attach the resilient pad to the boot shell, the main portion including an end region that extends into the heel-receiving opening, and the end region having an end edge including a notch configured for receipt of a calcaneus of the patient,
  a first medial strap attached to the boot shell and a first lateral strap attached to the boot shell and further comprising an instep pad having a first medial buckle configured for attachment to the first medial strap and a first lateral buckle configured for attachment to the first lateral strap, and
  a second medial strap attached to the boot shell and a second lateral strap attached to the boot shell and wherein the instep pad further includes a second medial buckle configured for attachment to the second medial strap and a second lateral buckle configured for attachment to the second lateral strap,
  wherein proximal ends of the first medial strap and the first lateral strap are attached to the calf portion of the boot shell and wherein proximal ends of the second medial strap and the second lateral strap are attached to a junction region of the boot shell where the sole portion and calf portion meet.

17. The surgical boot apparatus of claim 16, wherein the instep pad has a first pocket situated between the first medial buckle and the first lateral buckle, the first pocket has open sides, and distal ends of the first medial strap and the first lateral strap are insertable into the first pocket through the open sides of the first pocket to retain the distal ends of the first medial strap and the first lateral strap against the instep pad during surgery.

18. The surgical boot apparatus of claim 17, wherein the instep pad has a second pocket situated between the second medial buckle and the second lateral buckle, the second pocket has open sides, and distal ends of the second medial strap and the second lateral strap are insertable into the second pocket through the open sides of the second pocket to retain the distal ends of the second medial strap and the second lateral strap against the instep pad during surgery.

19. The surgical boot apparatus of claim 18, wherein the instep pad includes a leg-engaging portion that is generally hour glass shaped, a first patch coupled to the leg-engaging portion, and a second patch coupled to the leg-engaging portion, wherein the first pocket is defined between the first patch and the leg-engaging portion, and the second pocket is defined between the second patch and the leg-engaging portion.

* * * * *